US010182772B1

(12) United States Patent
Rotman et al.

(10) Patent No.: US 10,182,772 B1
(45) Date of Patent: Jan. 22, 2019

(54) SYSTEMS AND METHODS FOR OBJECT DETECTION FOR NUCLEAR MEDICINE IMAGING

(71) Applicant: General Electric Company, Schenectady, NY (US)

(72) Inventors: Elad Rotman, Haifa (IL); Ilan Levin, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/724,606

(22) Filed: Oct. 4, 2017

(51) Int. Cl.
*A61B 6/04* (2006.01)
*A61B 5/00* (2006.01)
*A61B 6/00* (2006.01)
*A61B 5/107* (2006.01)

(52) U.S. Cl.
CPC ............ *A61B 6/04* (2013.01); *A61B 5/0077* (2013.01); *A61B 5/1079* (2013.01); *A61B 6/4258* (2013.01); *A61B 6/488* (2013.01); *A61B 6/58* (2013.01)

(58) Field of Classification Search
USPC .............................. 250/492.3; 378/65, 68, 69
See application file for complete search history.

(56) References Cited

U.S. PATENT DOCUMENTS

| 9,717,461 | B2* | 8/2017 | Yu .......................... A61B 5/721 |
| 2008/0218743 | A1* | 9/2008 | Stetten ................. A61B 8/0833 356/73 |
| 2014/0193336 | A1* | 7/2014 | Rousso .............. A61K 51/0476 424/1.65 |
| 2015/0327831 | A1 | 11/2015 | Levin et al. |

* cited by examiner

*Primary Examiner* — Kiet T Nguyen
(74) *Attorney, Agent, or Firm* — Dean D. Small; The Small Patent Law Group, LLC

(57) ABSTRACT

Systems and methods described herein generally relate to object detection for nuclear medicine (NM) imaging. The systems and methods acquire triplets representing line of sights between a plurality of receive diodes and light emitting diodes (LEDs) positioned along a circumference of a gantry with respect to one or more objects of a patient. The systems and methods identify a number of the one or more objects based on a number of triplets for one of the LEDs. When a single object is identified, the systems and methods determine a shape of the single object based on a reference point within the single object and line of sights adjacent to the single object. Alternatively, when a plurality of objects are identified, the systems and methods utilize the line of sights to identify shapes of the plurality of objects.

20 Claims, 12 Drawing Sheets

SYSTEMS AND METHODS FOR OBJECT DETECTION FOR NUCLEAR MEDICINE IMAGING

FIELD

Embodiments described herein generally relate to object detection for nuclear medicine (NM) imaging.

BACKGROUND

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images.

However, during NM imaging motion from the patient affects the resultant image. During a scan of the patient multiple 2D slices are accumulated to form a 3D image of the patient. Objects of the patient need to be monitored during the scan to adjust for motion of the patient. For example, the objects need to detect the contour of the patient before the detectors approach the patient, and should be adjusted in case the patient moves during the scan. Conventional methods use forms of filtering and/or segmentation to identify a position of the objects extending a length of the scan. Alternatively, conventional systems use Computed Tomography (CT) during the scan, which exposes the patient to additional radiation.

BRIEF DESCRIPTION

In an embodiment, a method (e.g., for object detection of a patient) is provided. The method includes acquiring triplets representing line of sights between a plurality of receive diodes and light emitting diodes (LEDs) positioned along a circumference of a gantry with respect to one or more objects of a patient. The method includes identifying a number of the one or more objects based on a number of triplets for one of the LEDs. When a single object is identified, determining a shape of the single object based on a reference point within the single object and line of sights adjacent to the single object. Alternatively, when a plurality of objects are identified, utilizing the line of sights to identify shapes of the plurality of objects.

In an embodiment, a medical imaging system is provided. The medical imaging system includes plurality of diodes and light emitting diodes (LEDs) disposed about a circumference of a gantry. The system includes at least one processor that is operably coupled to the plurality of diodes and LEDs. The at least one processor configured to acquire triplets representing line of sights between the plurality of diodes and LEDs with respect to one or more objects. The at least one processor is configured to identify a number of the one or more objects based on a number of triplets for one of the LEDs. When a single object is identified the at least one processor is configured to determine a shape of the single object based on a reference point within the single object and line of sights adjacent to the single object. When a plurality of objects are identified the at least one processor is configured to utilize the lines of sights to identify shapes of the plurality of objects.

In an embodiment, a tangible and non-transitory computer readable medium is provided. The tangible and non-transitory computer readable medium includes one or more programmed instructions configured to direct one or more processors. The one or more processors are configured to acquire triplets representing line of sights between a plurality of diodes and light emitting diodes (LEDs) positioned along a circumference of a gantry with respect to one or more objects. The one or more processors are configured to identify a number of the one or more objects based on a number of triplets for one of the LEDs. When a single contour is identified, the one or more processors are configured to determine a shape of the single object based on a reference point within the single object and lines of sight adjacent to the single object. When a plurality of objects are identified, the one or more processors are configured to utilize the lines of sights to identify shapes of the plurality of objects.

DETAILED DESCRIPTION

Figure 1:
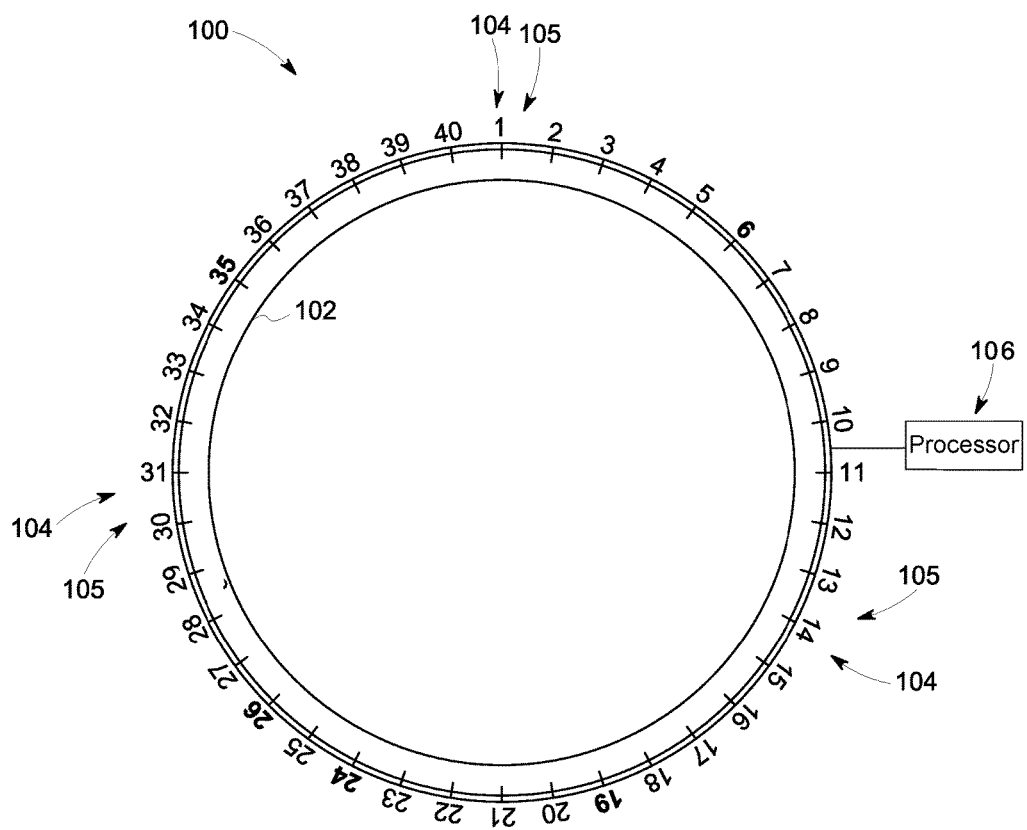
FIG. 1 shows a schematic view of an embodiment of a gantry of a medical imaging system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for object detection by a nuclear imaging (NM) system. The object can represent a body contour of a patient. The identification of the one or more objects is based on line of sights from photo-diodes and/or other light detectors such as photo transistors or photo resistors and light emitting diodes (LEDs) positioned along a circumference of a gantry. For example, 80 LEDs are positioned along an interior circumference of the gantry. The LEDs are interposed between a pair of diodes. The LEDs are activated sequentially (e.g., one at a time) along the circumference. One or more objects from the patient positioned within the gantry block the photons reaching some of the diodes. For example, a torso of the patient can block the photons emitted from the LED from being received by some of the diodes. A line of sight is formed when photons emitted by the LED are blocked by one of the objects. The line of sight represents the LED and the directly adjacent unblocked diode to the blocked diodes from the objects. For example, the line of sight is formed from two unblocked diodes that receive photons from the LED. The two unblocked diodes receive are directly adjacent to the diodes that are blocked by the objects. The line of sight if formed by the diodes that receive photons from the LED adjacent to the blocked diodes. The line of sight forms a triplet of three values, which represents a position of the LED and positions of the pair of diodes relative to the gantry receiving the photons from the LED. For example, the first value represents the LED, the second value represents a first receiving diode adjacent to a blocked diode, and the third value represents a second receiving diode adjacent to a blocked diode. The NM system determines a shape of the object based on the line of sights formed by the LEDs of the gantry. For example, the NM system analyzes positions of the line of sights relative to a reference position within the object to identify a polygon representing a shape of the object. Optionally, multiple objects are positioned within the gantry. For example, for two objects multiple line of sets are formed by a single LED. A first line of sight (e.g., triplet) is formed for a first object, and a second line of sight (e.g., triplet) is formed for a second object. Each of the triplets corresponding to the first and second line of sights includes the single LED.

A number of objects is determined by the NM system based on a number of triplets assigned to the single LED. For example, two objects are positioned within the gantry. When the LED emits photons, two different lines of sights are formed by two different pairs of diodes based on positions of the two objects. The NM system identifies shapes of the two objects based on the different triplets. The images are separated into two distinct portions. A first portion positioned outside the contour (e.g., not blocked) represents a zero, and a second portion positioned within the contour represents (e.g., blocked) a one. The NM system adds the images together to identify the shapes of the two objects.

Additionally or alternatively, one of the objects can be too small, such as less than two centimeters. For example, one of the images formed by the triplets may not include a line of sight for the small object. During the graphically summing and/or adding the images, which may remove the small object. The NM system identifies the small object by identifying the lines of sights blocked by the small object. The NM system identifies intersections between the lines of sights within the small object. A shape and/or position of the small object is determined by overlaying a predetermined radius on the intersections sequentially. For example, the NM system compares different positions of the predetermined radius, and identifies a select position when the predetermined radius includes a higher number of intersections relative to alternative positions. The NM system determines the select position of the small object based on a number of intersections within the predetermined radius.

A technical effect of at least one embodiment includes improving the motion plan and parameters for trans-axial reconstruction.

Figure 13:
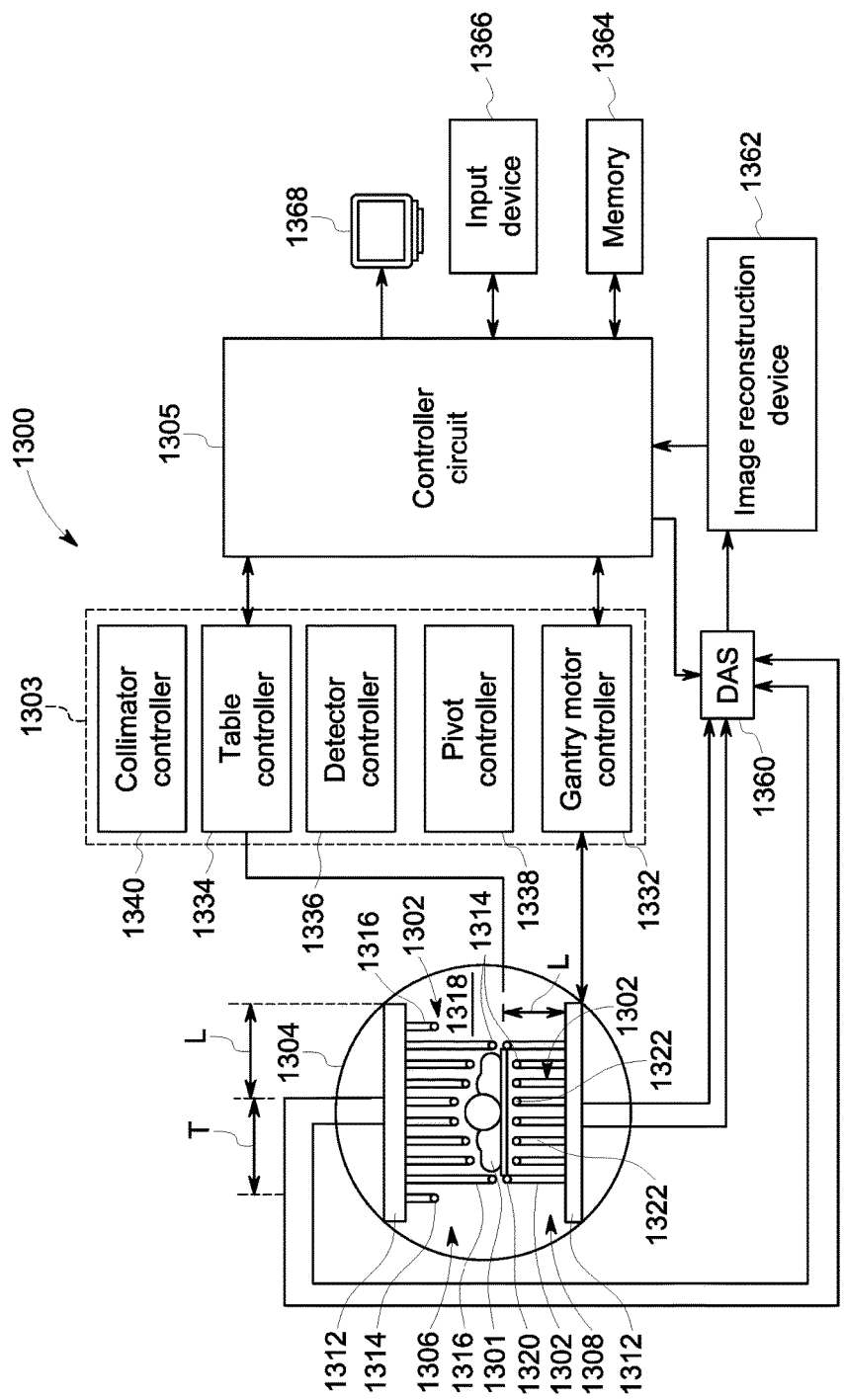
FIG. 13 illustrates an embodiment of a medical imaging system.

FIG. 1 shows a schematic view of an embodiment of a gantry 100 of a medical imaging system (e.g., the medical imaging system 1300 of FIG. 13). The gantry 100 is operably coupled to at least one processor 106 106 (e.g., the controller circuit 1305). The gantry 100 is shown having a plurality of LEDs 104 and receive diodes 105 along a circumference 102 of the gantry 100. It may be noted that the gantry 100 may have a different shape that is non-circular than what is shown in FIG. 1. The gantry 100 illustrates 40 LEDs 104 interposed between 120 receive diodes 105 (not shown). Additionally or alternatively, additional LEDs 104 (e.g., 80 LEDs) and/or receive diodes 105 (e.g., 160 diodes) may be positioned along a circumference 102 of the gantry 100.

The at least one processor 106 is configured to instruct the LEDs 104 to sequentially emit photons along the circumference 102 of the gantry 100. For example, the LEDs 104 may emit photons one at a time along the circumference 102 from LED 104 at position 1. The at least one processor 106 receives signals from the receive diodes 105 indicating that the photons were received. Subsequently, the at least one processor 106 instructs the LED 104 at position 2 to emit photons. The at least one processor 106 continues the process through the LEDs along the circumference 102 of the gantry 100. The at least one processor 106 forms a triplet representing a line of sight based on the receive diodes 105 blocked by the at least one object. For example, the at least one processor 106 identifies the receive diodes 105 obstructed by the at least one object. The at least one processor 106 selects the receive diodes 105 that are adjacent to the obstructed receive diodes 105, which receive the photons as a part of the triplet. The triplet includes three values. The first value is the LED 104 emitting the photons, and the second and third values represent the receive diodes 105 adjacent to the obstructed receive diodes 105. The triplet indicates a position of the LED 104 and receive diodes 105 along the gantry 100 forming the line of sight.

Figure 2:
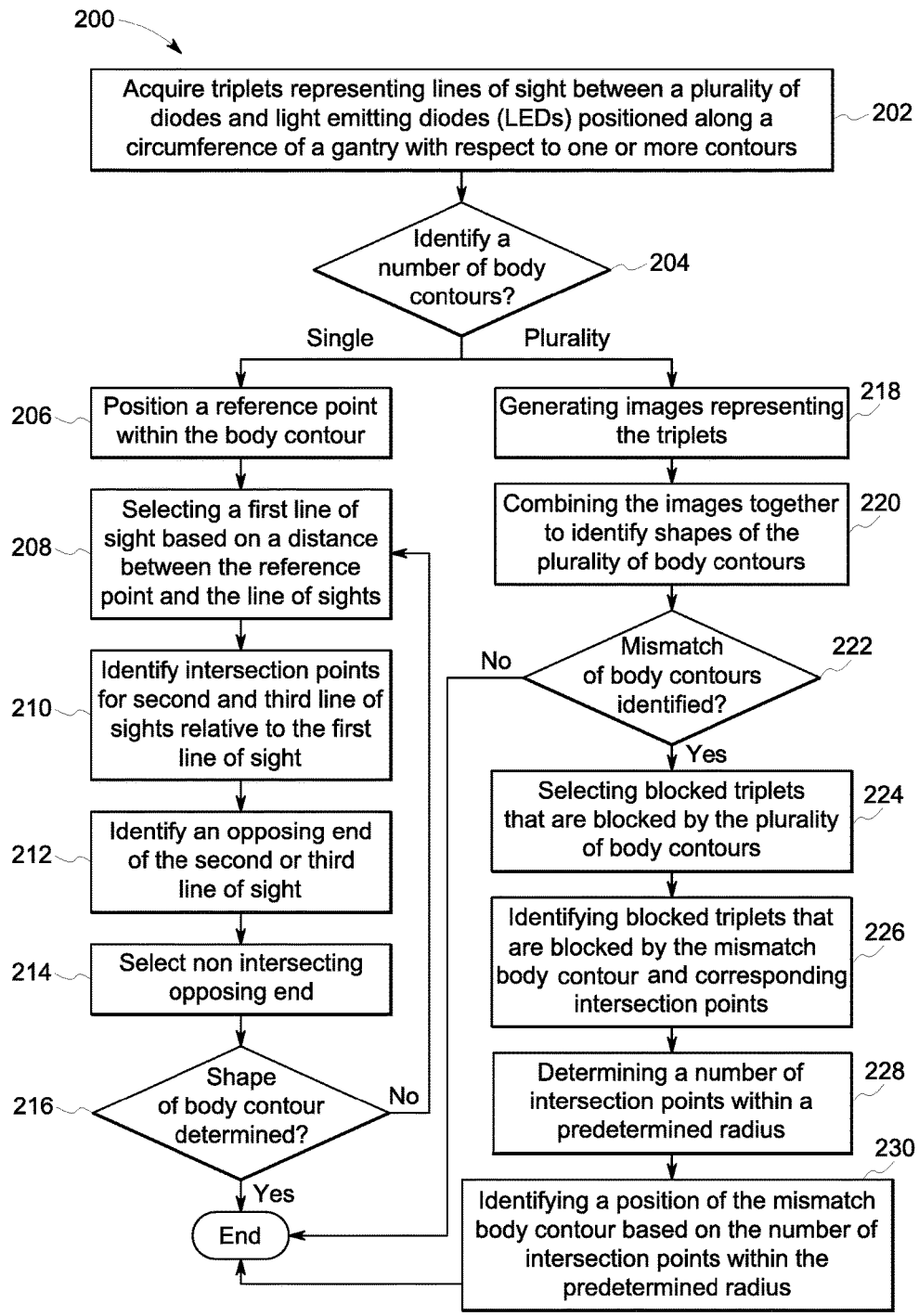
FIG. 2 illustrates a flow chart of an embodiment of a method for object detection of a patient.

FIG. 2 illustrates a flow chart of an embodiment of a method 200 for object detection of a patient. The method 200, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein.

Beginning at 202, the at least one processor 106 acquires triplets representing lines of sight between a plurality of receive diodes 105 and LEDs 104 positioned along the circumference 102 of the gantry 100 with respect to one or more objects. For example, the at least one processor 106 instructs the LEDs 104 to emit photons sequentially along the circumference 102 of the gantry 100. The at least one processor 106 identifies the plurality of receive diodes 105 that receive the photons. The at least one processor 106 determines the receive diodes 105 that are adjacent to the obstructed receive diodes 105 by the at least one object.

Figure 3:
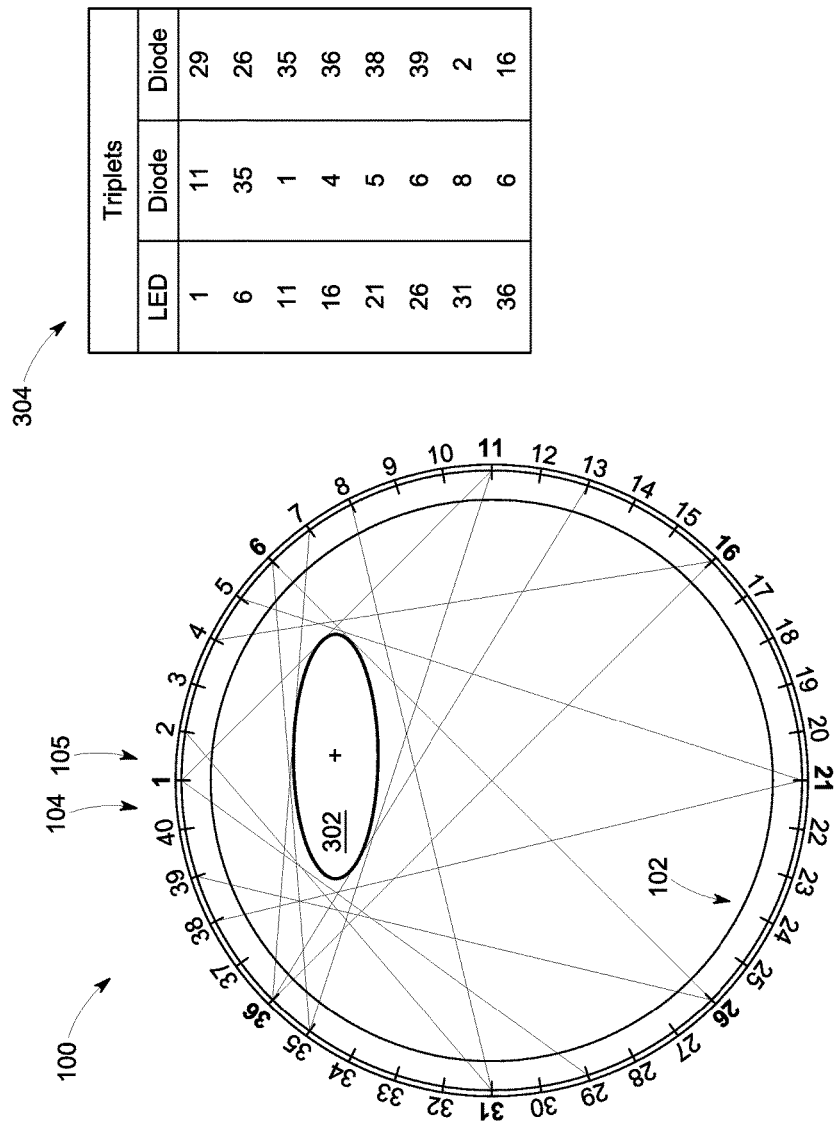
FIG. 3 illustrates an embodiment of a single object within a gantry.

FIG. 3 illustrates an embodiment of a single object 302 within the gantry 100. The at least one processor 106 instructs the LED 104 at position 1 to emit photons. The at least one processor 106 receives signals from the receive diodes 105 indicating the receive diodes 105 that receive photons emitted by the LED 104. The at least one processor 106 does not receive a signal from the receive diodes 105 at positions 12-28 along the gantry 100. For example, the photons from the LED 104 at position 1 are blocked by the object 302 for the receive diodes 105 at positions 12-28. The plurality of receive diodes 105 adjacent to the blocked receive diodes 105 at positions 11 and 29 receive the photons from the LED 104. The at least one processor 106 defines the triplet representing the line of sight as the LED 104 at position 1, the diode 105 at position 11, and the diode 105 at position 29.

The at least one processor 106 continues to instruct the LEDs 104 to emit photons one at a time along the circumference to define additional line of sights or triplets. For example, the at least one processor 106 defines a set of triplets as shown in a table 304. The table 304 indicates a number of triplets identified by the at least one processor 106.

Figure 7:
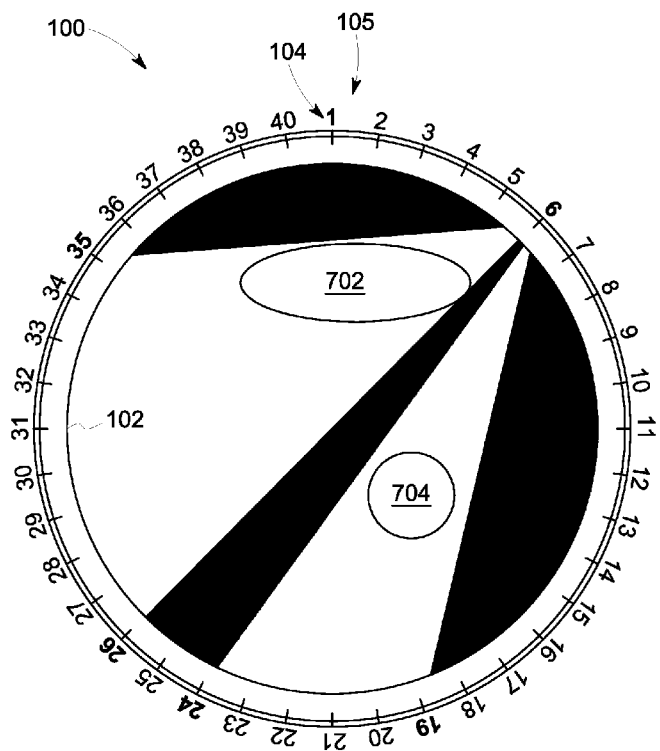
FIG. 7 illustrates an embodiment of a plurality of objects within a gantry.

At 204, the at least one processor 106 determines a number of objects. The number of objects within the gantry 100 is determined based on a number of triplets for each LED 104. For example, when a plurality of objects are positioned within the gantry 100, at least one LED 104 will have at least two triplets (for example as shown in FIG. 7). As shown in the table 304, each LED 104 is shown having a single triplet. The at least one processor 106 determines that only a single object 302 is present within the gantry 100.

Figure 4:
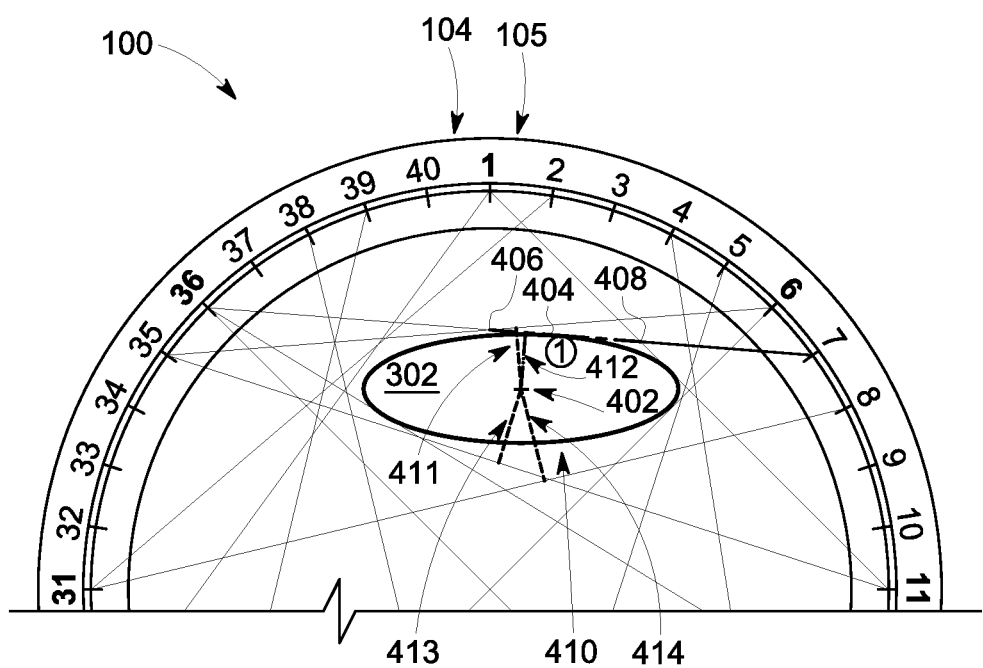
FIG. 4 illustrates an embodiment of a reference point and a first line of sight with respect to a single object.

At 206, the at least one processor 106 positions a reference point within the object 302. FIG. 4 illustrates an embodiment of a reference point 402 and a first line of sight 404 with respect to the single object 302. It may be noted the reference point 402 is within the object 302. The reference point 402 can be identified by the at least one processor 106 based on geometries of the medical imaging system (e.g., the medical imaging system 1300). For example, a position of the patient within the gantry 100 is based on a patient table height relative to the gantry 100. When the patient is imaged by the medical imaging system, the patient traverses through the gantry via the patient table. The at least one processor 106 determines a position of the patient table height within the gantry 100. Based on the table height, the at least one processor 106 can determine an approximate position of the patient within the gantry 100. The at least one processor 106 positions the reference point 402 within the position. Additionally or alternatively, the at least one processor 106 may position the reference point 402 based on a gap of the line of sights formed by the triplets. For example, the at least one processor 106 plots the line of sights based on the table 304 (FIG. 3). The at least one processor 106 identifies a gap 410 formed between the line of sights and positions the reference point 402 within the gap 410.

At 208, the at least one processor 106 selects the first line of sight 404 based on a distance between the reference point 402 and the line of sights. For example, the at least one processor 106 plots the line of sights based on the table 304. The at least one processor 106 calculates distances 411-414 between the line of sights and the reference point 402. The at least one processor 106 compares the distances 411-414 with each other to identify a shorter distance 411-414 relative to each other. The at least one processor 106 identifies the distance 412 being smaller and/or shorter relative to the remaining distances 411, 413-414. The distance 412 corresponds to the first line of sight 404 formed by the triplet (36, 6, 16), and is selected by the at least one processor 106.

At 210, the at least one processor 106 identifies intersection points 406, 408 for second and third line of sights relative to the first line of sight 404. The intersection points 406, 408 represent boundaries of the first line of sight 404. For example, the intersection points 406, 408 correspond to positions of alternative line of sights that bound the first line of sight 404. The intersection points 406, 408 can be identified by the at least one processor 106 by plotting the line of sights within the gantry. The intersection points 406, 408 are utilized by the at least one processor 106 to identify the second and third line of sights 502, 504 as shown in FIG. 5.

Figure 5:
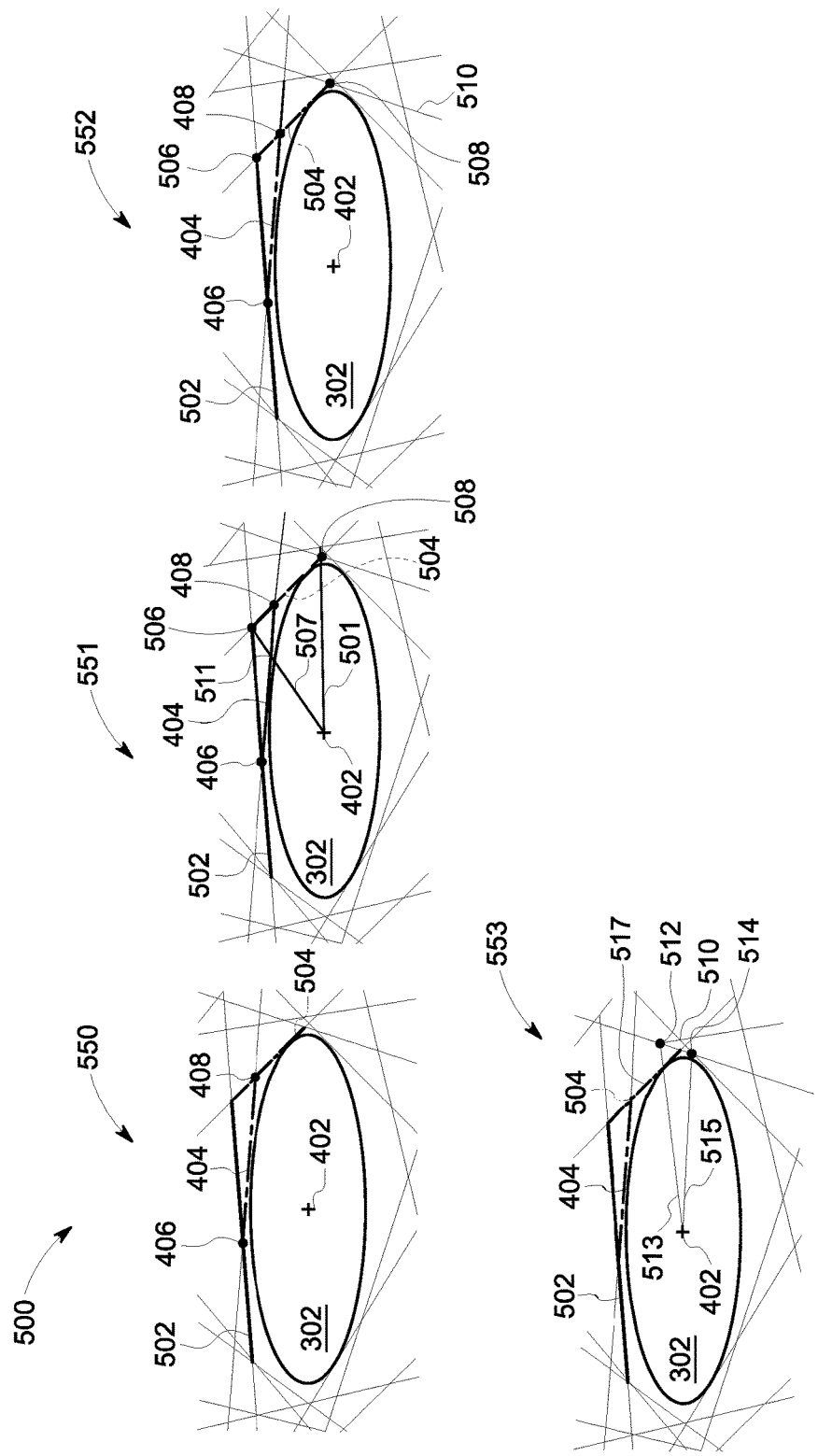
FIG. 5 illustrates an embodiment of a portion of a process to determine a shape of a single object.

FIG. 5 illustrates an embodiment of a portion of a process 500 to determine a shape of the single object 302. As shown at 550, the intersection points 406, 408 of the first line of sight 404 intersect two different line of sights. The at least one processor 106 selects the two different line of sights as the second line of sight 504, and the third line of sight 510. For example, the intersection points 406, 408 correspond to the third or second line of sights 502, 504, respectively.

At 212, the at least one processor 106 identifies opposing ends of the second or third line of sights 504, 502. For example, the at least one processor 106 selects one of the second or third line of sights 504, 502. As shown at 551, the at least one processor 106 selects the second line of sight 504. The at least one processor 106 identifies the opposing ends 506, 508 of the second line of sight 504. The opposing ends 506, 508 represent intersection points from alternative line of sights. For example, the opposing end 506 is bounded by the first line of sight 404. The opposing end 508 is bounded by a fourth line of sight 510.

At 214, the at least one processor 106 selects a non-intersecting opposing end. As shown in 551, the at least one processor 106 selects one of the opposing ends 506, 508 that does not intersect with the first line of sight 404. For example, the at least one processor 106 forms lines 507, 509 from the reference point 402 to each of the opposing ends 506, 508. The at least one processor 106 determines whether the lines 507, 509 intersect with the first line of sight 404. For example, the line 507 is formed from the reference point 402 to the opposing end 506. The line 507 crosses the first line of sight 404 at 511. In another example, the line 509 is formed from the reference point 402 to the opposing end 508. The line 509 does not cross the first line of sight 404. Since the opposing end 509 does not intersect with the first line of sight 404, the at least one processor 106 selects the opposing end 508.

At 216, the at least one processor 106 determines whether a shape of the single object 302 is formed. For example, the at least one processor 106 determines whether a polygon is formed around the reference point 402. If the polygon is not formed, then the at least one processor 106 repeats the portion of the process 500 shown in FIG. 5.

For example, at 552, the at least one processor 106 selects the fourth line of sight 510 at the opposing end 509. At 553, the at least one processor 106 identifies opposing ends 512, 514 of the fourth line of sight 510. The opposing ends 512, 514 are bounded by alternative line of sights. The at least one processor 106 selects one of the opposing ends 512, 514 that does not intersect with the second line of sight 504. For example, the at least one processor 106 forms lines 513, 515 from the reference point 402 to each of the opposing ends 512, 514. The line 513 crosses the second line of sight 504 at 517. In another example, the line 515 does not cross the second line of sight 504. Since the opposing end 514 does not intersect with the second line of sight 504, the at least one processor 106 selects the opposing end 514. The at least one processor 106 repeats the process for the lines of sight around the object 502 until a polygon is formed.

Figure 6:
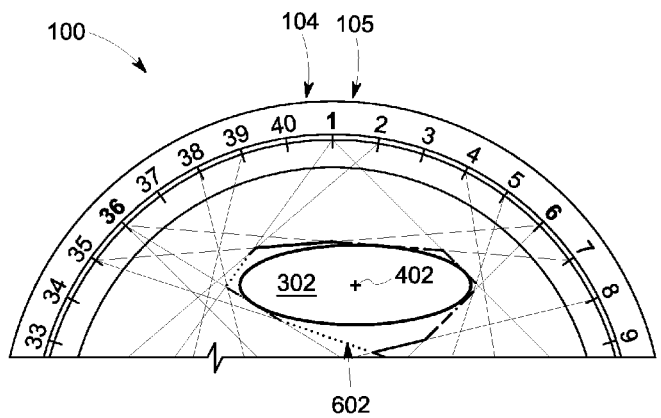
FIG. 6 illustrates an embodiment of a polygon representing a shape of a single object.

FIG. 6 illustrates an embodiment of a polygon 602 representing a shape of the single object 302. The polygon 602 is formed based on the line of sights proximate to the object 302. The polygon 602 encloses the reference point 402.

Returning to 204, the at least one processor 106 determines a plurality of objects within the gantry 100 based on a number of triplets for one of the LED 104. FIG. 7 illustrates an embodiment of a plurality of objects 702, 704 within the gantry 100. The at least one processor 106 instructs the LED 104 at position 6 to emit photons. The photons are received by the receive diodes 105 at positions 19, 24, 26, 35. The at least one processor 106 assigns a first triplet for the LED 104 at position 6 as (6, 19, 24) and a second triplet for the LED 104 at position 6 as (6, 26, 35). The at least one processor 106 determines that one of the LEDs 104 of the gantry 100 includes two triplets. Since one of the LEDs 104 includes two triplets, the at least one processor 106 determines that a plurality of objects are within the gantry 100. The at least one processor 106 utilizes the line of sights identify shapes of the plurality of objects.

Figure 8:
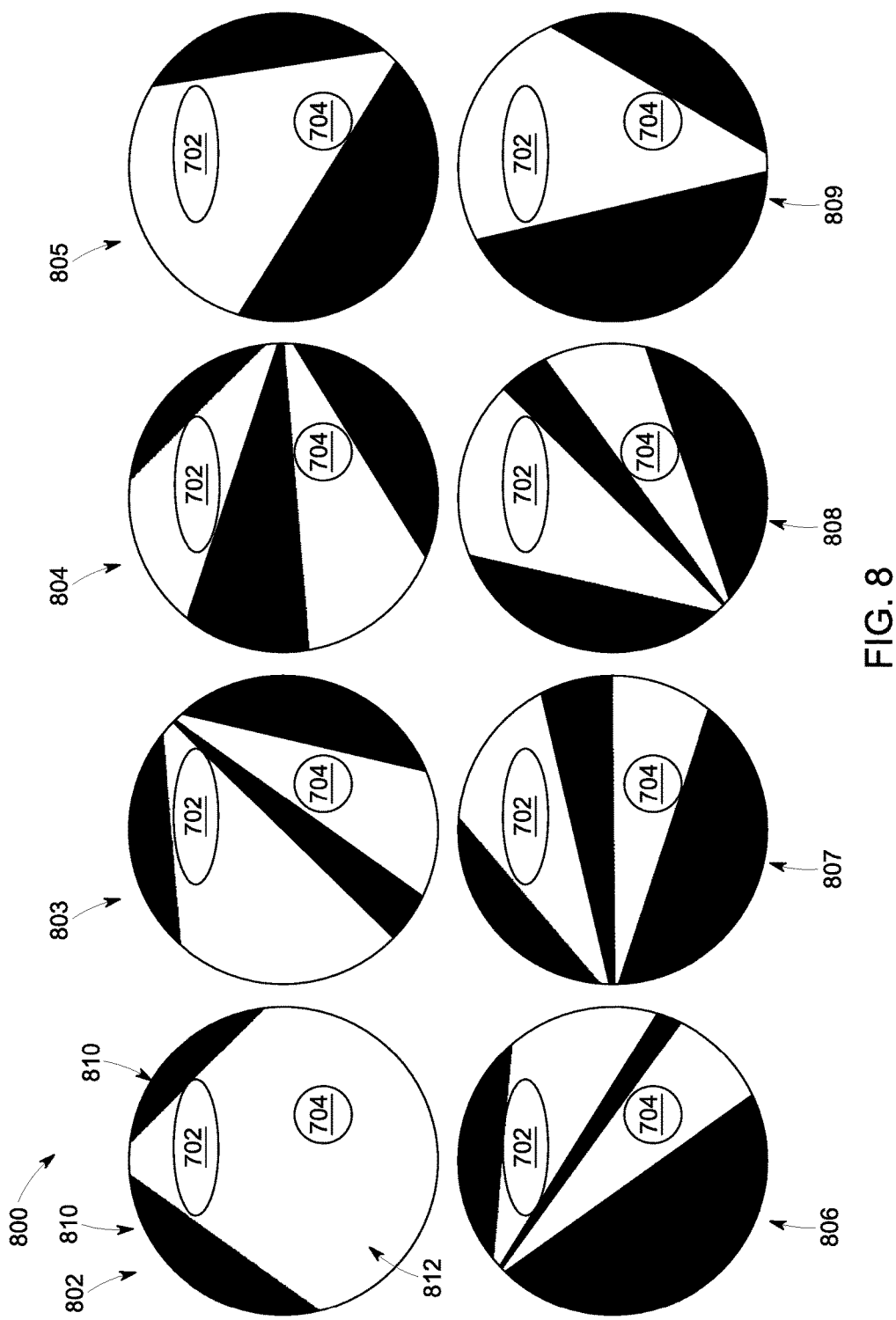
FIG. 8 illustrates an embodiment of images representing triplets.

At 218, the at least one processor 106 generates images representing the triplets. FIG. 8 illustrates an embodiment of images 800 representing triplets 802-809. The images 800 of the triplets 802-809 are shown having two separate colors. The separate colors are utilized for the graphically summing and/or adding operation at 220. The separate colors are determined based on a position of the plurality of objects 702, 704. For example, the portion of the triplet 802 outside 810 the plurality of objects 702, 704 have a value of zero by the at least one processor 106, which is shown as black. In another example, the portion of the triplet 802 within 812 the plurality of objects 702, 704 have a value of one by the at least one processor 106, which is shown as white. The portions within 812 the plurality of objects 702, 704 correspond to the receive diodes 105 that are blocked by the plurality of objects 702, 704. Alternatively, the portions outside 810 the plurality of objects 702, 704 correspond to the receive diodes 105 that receive photons from the LEDs 104.

At 220, the at least one processor 106 combines the images together to identify shapes of the plurality of objects 702, 704. For example, the at least one processor 106 utilizes the line of sights to identify shapes of the plurality of objects 702, 704. The at least one processor 106 performs an "and" operation on the triplets 802-809. For example, the portion of the triplets 802-809 that have a value of one (e.g., white portion) remains. Alternatively, the portion of the triplets 802-809 that have a value of zero (e.g., black portion) remains black. A mixed portion that includes adding both white and black only the black portion remains.

Figure 9:
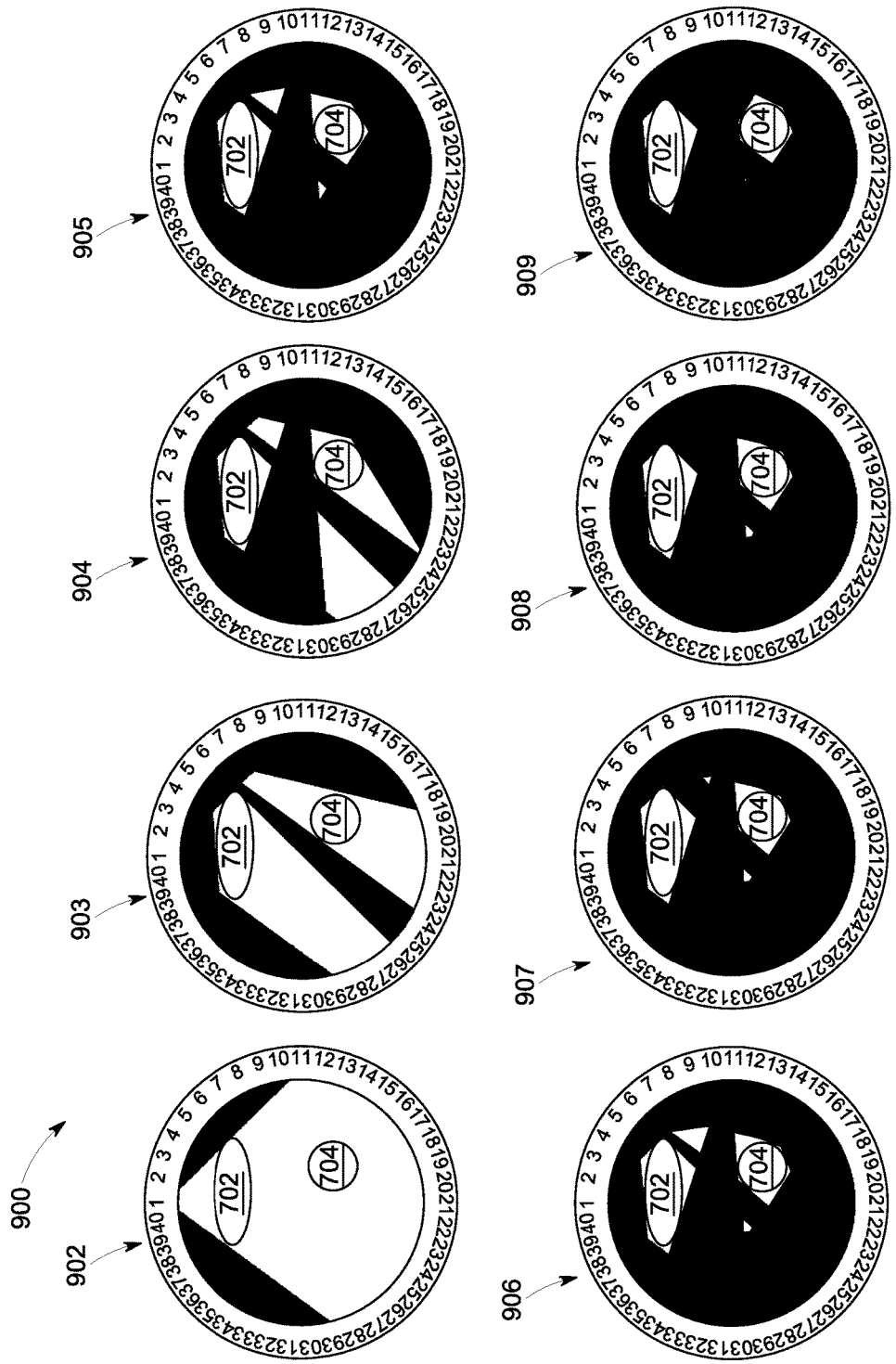
FIG. 9 illustrates an embodiment of adding the images of FIG. 8.

FIG. 9 illustrates an embodiment 900 of adding the images 800. For example, the at least one processor 106 graphically sums the triplets 802-809 together. The image 902 corresponds to the triplet 802. The image 904 corresponds to the adding of the triplets 802, 803. For example, the portion representing a value of zero is expanded relative to the image 902 based on the triplet 803. The at least one processor 106 continually adds the triplets 802-809 together to form the image 909. The image 909 represents the addition of the triplets 802-809. For example, the image 909 forms two different shapes of the plurality of objects 702, 704. The shapes represent polygons for the objects 702, 704.

At 222, the at least one processor 106 identifies if there is a mismatch of objects. The mismatch of objects is present when a number of polygons does not match a number of objects. For example, the at least one processor 106 identifies two polygons in the image 909. The at least one processor 106 compares the number of polygons with the number of triplets for each of the LEDs 104. For example, the at least one processor 106 identified the LED 104 at position 6 includes two triplets. Based on the two triplets, the at least one processor 106 determines two objects are present within the gantry 100. The at least one processor 106 compares the number of polygons of image 909 with the number of triplets for the LED 104 at position 6. The at least one processor 106 determines that the number of polygons and the number of triplets match. The at least one processor 106 determines that there is not a mismatch.

Figure 10:
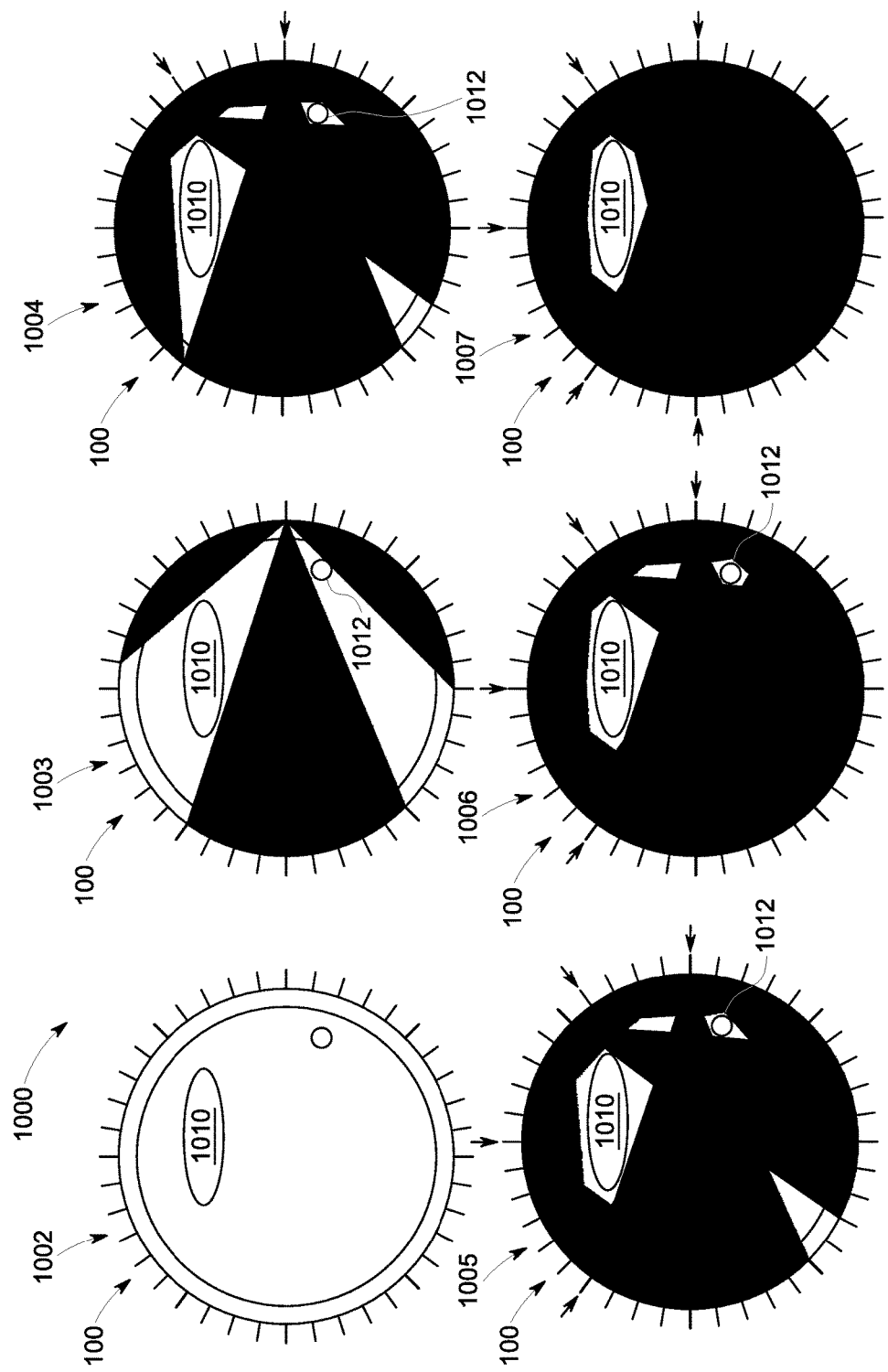
FIG. 10 illustrates an embodiment of a mismatch contour.

FIG. 10 illustrates an embodiment of a mismatch contour 1000. For example, the at least one processor 106 graphically sums the images 1002-1007 together. For example, in image 1002 shows two objects 1010, 1012 within the gantry 100. Image 1003 shows two triplets from one of the LEDs 104. Based on the two triplets for a single LED 104, the at least one processor 106 identifies two objects within the gantry 100. As shown in FIGS. 8-9, the at least one processor 106 generates images of the triplets and adds them together. The triplets include a portion that represents zero (e.g., not blocked by the objects 1010, 1012) and a portion that represents one (e.g., block by the objects 1010, 1012). The at least one processor 106 adds the images together to form the image 1007. The object 1012 is small relative to the object 1010. For example, the object 1012 has a diameter that is less than 1.7 centimeters. Based on a size of the object 1012, one of the triplets includes an LED having a single triplet. For example, one of the images generated by the at least one processor 106 does not include a portion that is block by the object 1012. When the at least one processor 106 adds the images of the triplets together, the object 1012 is missing and/or removed for the image 1007. For example, only a single polygon is generated for the object 1010. The at least one processor 106 compares the number of polygons with the number of triplets for each of the LEDs 104. The at least one processor 106 identifies a mismatch. For example, at least one LED 104 includes two triplets, while only a single polygon is identified.

It may be noted that the diameter of the object 1012 can be reduced. For example, additional LEDs 104 and receive diodes 105 may be positioned along a circumference 102 of the gantry 100. However, this may add additional costs and processing time.

Figure 11:
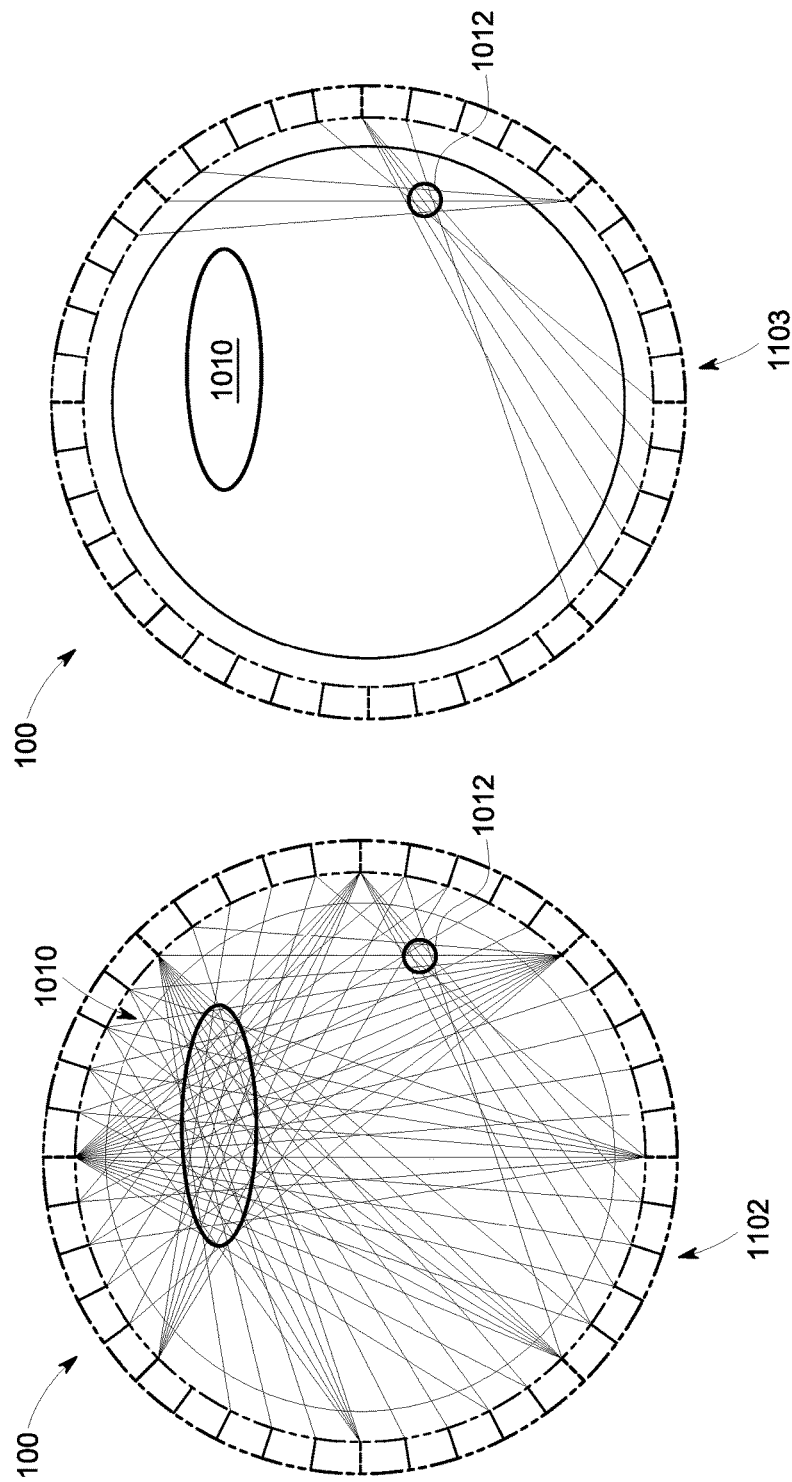
FIG. 11 illustrates an embodiment of triplets that are blocked by a plurality of contours.

When a mismatch of the objects is identified, then at 224, the at least one processor 106 selects blocked triplets that are block by the plurality of objects 1010, 1012. FIG. 11 illustrates an embodiment of triplets that are blocked by the plurality of contours 1010, 1012. For example, the image 1102 shows all of the triplets blocked by the objects 1010, 1012. The triplets blocked by the objects 1010, 1012 are identified by the at least one processor 106 by selecting the lines of sights between the LEDs 104 and the receive diodes 105 that are not included in the triplets.

At 226, the at least one processor 106 identifies the blocked triplets that are blocked by the mismatch object 1012 and corresponding intersection points. For example, the at least one processor 106 may compare a position of the polygon in the image 1007 (FIG. 10) with the image 1102. The polygon corresponds to the object 1010, which is not the mismatch object 1012. The at least one processor 106 identifies the blocked triplets that correspond to the position of the polygon and removes the blocked triplets to form the image 1103. The blocked triplets within the image 1103 are only for the mismatch object 1012.

Figure 12:
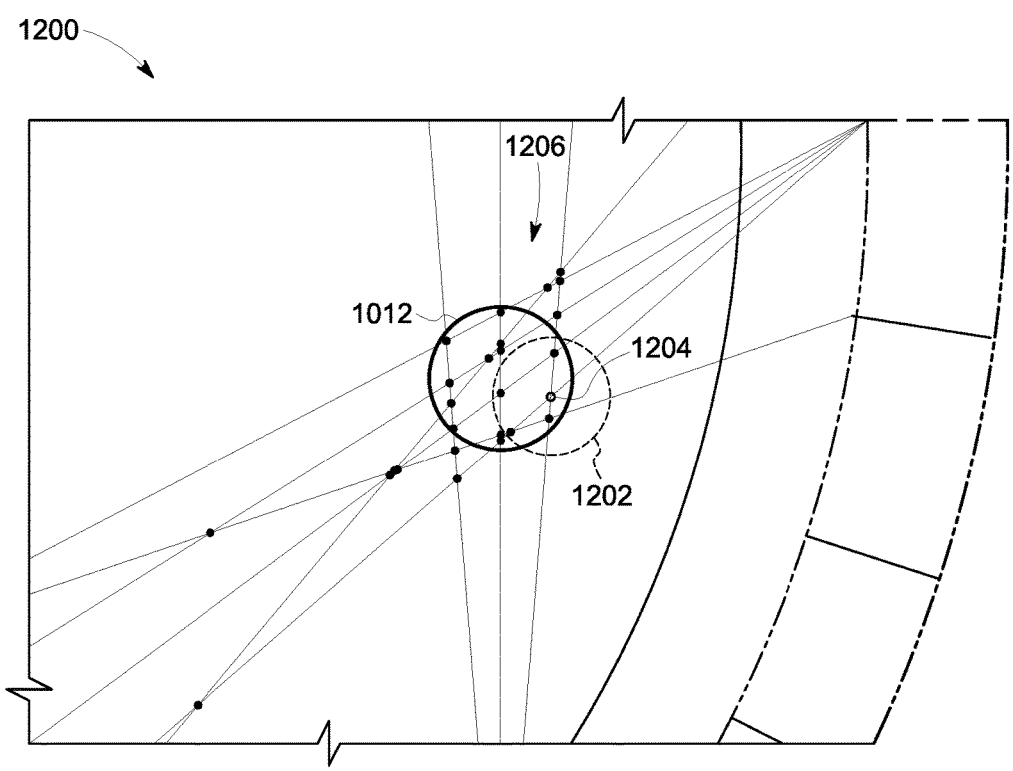
FIG. 12 illustrates an embodiment of blocked triplets that are blocked by a mismatch object.

FIG. 12 illustrates an embodiment 1200 of blocked triplets that are blocked by the mismatch object 1012. The blocked triplets intersect with each other to form the intersection points 1206. The intersection points 1206 are positioned proximate to the mismatch object 1012.

At 228, the at least one processor 106 determines a number of intersection points 1206 within a predetermined radius 1202. For example, the at least one processor 106 centers the predetermined radius 1202 on each of the intersection points 1206. The predetermined radius 1202 may represent a diameter of 1 centimeter. Additionally or alternatively, the diameter may be larger than 1 centimeter.

FIG. 12 shows the predetermined radius 1202 centered at one of the intersection points 1206, the intersection point 1204. The at least one processor 106 counts a number of the intersection points 1206 within the predetermined radius 1202. For example, as shown in FIG. 12, the predetermined radius 1202 includes four intersection points 1206. The at least one processor 106 continually compares a number of intersection points 1206 between the different positions of the predetermined radius 1202.

At 230, the at least one processor 106 determines a position of the mismatch object 1012 based on the number of intersection points 1206 within the predetermined radius 1202. The position of the mismatch object 1012 corresponds to a position that includes a higher number of intersection points 1206 within the predetermined radius 1202. For example, the at least one processor 106 selects the position of the mismatch object 1012 that includes a higher number of intersection points 1206 relative to other positions of the predetermined radius 1202.

The at least one processor 106 may compare a position of the one or more objects during the scan. For example, the at least one processor 106 determines motion of the patient based on a position of the one or more objects overtime during the scan. Based on a position of the one or more objects, the at least one processor 106 can adjust and/or configure a response of the medical imaging system (e.g., a medical imaging system 1300 of FIG. 13).

For example, the at least one processor 106 determines a position of at least one object proximate to the gantry 100 and/or one or more imaging detectors (e.g., imaging detectors 1302 of FIG. 13). The at least one processor 106 may adjust a position of the one or more imaging detectors and/or a position of the patient table based on the position of the at least one object. The adjusted position of the one or more imaging detectors and/or the position of the patient table by the at least one processor 106 prevents a collision of the at least one object and/or patient.

In another example, the at least one processor 106 determines a difference in a first and second position of at least one object during the scan. The at least one processor 106 determines a distance of the at least one object between the first and second position. The at least one processor 106 compare the distance with a non-zero predetermined threshold. The non-zero predetermined threshold represents a magnitude that can result in a blurred image based on the movement of the at least one object during the scan. The at least one processor 106 may instruct the medical imaging system to stop the data acquisition of the patient. Additionally or alternatively, the at least one processor 106 may instruct the medical imaging system to restart data acquisition of the patient, since the movement causes the data acquisition is insufficient for producing an image.

In another example, the at least one processor 106 may subdivide the image acquisition of the patient based on when the motion occurred. The at least one processor 106 compares positions of at least one object during the scan to determine a distance between the positions. The at least one processor 106 separates the scan based on the distance between the positions. For example, the at least one processor 106 identifies distances of the at least one object during the scan. The at least one processor 106 identifies when the distances are above the non-zero predetermined threshold. The at least one processor 106 divides the data acquisition based on the distances of the at least one object during the scan.

For example, during the scan a first time period the distance between the positions of the at least one objects is less than the non-zero predetermined threshold, and during a second time period the distance between the positions of the at least one object is more than the non-zero predetermined threshold. The at least one processor 106 subdivides the data acquisition based on the motion and/or distance of the at least one object, and reconstructs the subdivided data acquisition. Optionally, the at least one processor 106 reconstructs (e.g., form medical images) the subdivided data acquisition separately. For example, prior to the motion (e.g., during the first time period) the at least one processor 106 receives a first set of the data acquisition. The at least processor reconstructs the first set of the data acquisition. After the motion (e.g., during the second time period) the at least one processor 106 receives a second set of the data acquisition. The at least processor reconstructs the second set of the data acquisition.

FIG. 13 illustrates an embodiment of a medical imaging system 1300. The medical imaging system 1300 includes a plurality of imaging detector head assemblies mounted on a gantry 1304 (which may be mounted, for example, in rows, in an iris shape, or other configurations, such as a configuration in which the movable detector carriers 1316 are aligned radially toward the patient-body 1301). The gantry 1304 may be similar to and/or the same as the gantry 100 shown in FIG. 1. It should be noted that the arrangement of FIG. 13 is provided by way of example for illustrative purposes, and that other arrangements (e.g., detector arrangements) may be employed in various embodiments. In the illustrated example, a plurality of imaging detectors 1302 are mounted to the gantry 1304. In the illustrated embodiment, the imaging detectors 1302 are configured as two separate detector arrays 1306 and 1308 coupled to the gantry 1304 above and below a subject 1301 (e.g., a patient), as viewed in FIG. 13. The detector arrays 1306 and 1308 may be coupled directly to the gantry 1304, or may be coupled via support members 1312 to the gantry 1304 to allow movement of the entire arrays 1306 and/or 1308 relative to the gantry 1304 (e.g., transverse translating movement in the left or right direction as viewed by arrow T in FIG. 1). Additionally, each of the imaging detectors 1302 includes a detector unit 1314, at least some of which are mounted to a movable detector carrier 1316 (e.g., a support arm or actuator that may be driven by a motor to cause movement thereof) that extends from the gantry 1304. In some embodiments, the detector carriers 1316 allow movement of the detector units 1314 towards and away from the subject 1301, such as linearly. Thus, in the illustrated embodiment the detector arrays 1306 and 1308 are mounted in parallel above and below the subject 1301 and allow linear movement of the detector units 1314 in one direction (indicated by the arrow L), illustrated as perpendicular to the support member 1312 (that are coupled generally horizontally on the gantry 1304). However, other configurations and orientations are possible as described herein. It should be noted that the movable detector carrier 1316 may be any type of support that allows movement of the detector units 1314 relative to the support member 1312 and/or gantry 1304, which in various embodiments allows the detector units 1314 to move linearly towards and away from the support member 1312.

Each of the imaging detectors 1302 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1302 may include one or more detector units 1314 coupled to a respective detector carrier 1316 and having dimensions of, for example, 4 cm to 20 cm and may be formed of Cadmium Zinc Telluride (CZT) tiles or modules. For example, each of the detector units 1314 may be 8×8 cm in size and be composed of a plurality of CZT pixelated modules (not shown). For example, each module may be 4×4 cm in size and have 16×16=256 pixels (pixelated anodes). In some embodiments, each detector unit 1314 includes a plurality of modules, such as an array of 1×7 modules. However, different configurations and array sizes are contemplated including, for example, detector units 1314 having multiple rows of modules.

It should be understood that the imaging detectors 1302 may be different sizes and/or shapes with respect to each other, such as square, rectangular, circular or other shape. An actual field of view (FOV) of each of the imaging detectors 1302 may be directly proportional to the size and shape of the respective imaging detector.

The gantry 1304 may be formed with an aperture 1318 (e.g., opening or bore) therethrough as illustrated. A patient table 1320, such as a patient bed, is configured with a support mechanism (not shown) to support and carry the subject 1301 in one or more of a plurality of viewing positions within the aperture 1318 and relative to the imaging detectors 1302. Alternatively, the gantry 1304 may comprise a plurality of gantry segments (not shown), each of which may independently move a support member 1312 or one or more of the imaging detectors 1302.

The gantry 1304 may also be configured in other shapes, such as a "C", "H" and "L", for example, and may be rotatable about the subject 1301. For example, the gantry 1304 may be formed as a closed ring or circle, or as an open arc or arch which allows the subject 1301 to be easily accessed while imaging and facilitates loading and unloading of the subject 1301, as well as reducing claustrophobia in some subjects 1301. Additional imaging detectors (not shown) may be positioned to form rows of detector arrays or an arc or ring around the subject 1301. By positioning multiple imaging detectors 1302 at multiple positions with respect to the subject 1301, such as along an imaging axis (e.g., head to toe direction of the subject 1301) image data specific for a larger FOV may be acquired more quickly. Each of the imaging detectors 1302 has a radiation detection face, which is directed towards the subject 1301 or a region of interest within the subject.

The collimators 1322 (and detectors) in FIG. 13 are depicted for ease of illustration as single collimators in each detector head. It may be noted that different types of collimators may be used in different columns. Optionally, for embodiments employing one or more parallel-hole collimators, multi-bore collimators may be constructed to be registered with pixels of the detector units 1314, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1303 may control the movement and positioning of the patient table 1320, imaging detectors 1302 (which may be configured as one or more arms), gantry 1304 and/or the collimators 1322 (that move with the imaging detectors 1302 in various embodiments, being coupled thereto). A range of motion before or during an acquisition, or between different image acquisitions, is set to maintain the actual FOV of each of the imaging detectors 1302 directed, for example, towards or "aimed at" a particular area or region of the subject 1301 or along the entire subject 1301. The motion may be a combined or complex motion in multiple directions simultaneously, concurrently, or sequentially.

The controller unit 1303 may have a gantry motor controller 1332, table controller 1334, detector controller 1336, pivot controller 1338, and collimator controller 1340. The gantry motor controller 1332 may move the imaging detectors 1302 with respect to the subject 1301, for example, individually, in segments or subsets, or simultaneously in a fixed relationship to one another. For example, in some embodiments, the gantry controller 1332 may cause the imaging detectors 1302 and/or support members 1312 to move relative to or rotate about the subject 1301, which may include motion of less than or up to 180 degrees (or more).

The controllers 1303, 1332, 1334, 1336, 1338, 1340 may be automatically commanded by a controller circuit 1305, manually controlled by an operator, or a combination thereof. Additionally, the controller circuit 1305 receives user inputs (e.g., control commands) from a user input device 1366, which is provided to receive user inputs (e.g., control commands), as well as a display 1368 to display images. The controller circuit 1305 is configured to control the operation of the medical imaging system 1300. The controller circuit 1305 may include one or more processors. Optionally, the controller circuit 1305 may include a central processing unit (CPU), one or more microprocessors, at least one processor, a graphics processing unit (GPU), or any other electronic component capable of processing inputted data according to specific logical instructions. Optionally, the controller circuit 1305 may include and/or represent one or more hardware circuits or circuitry that include, are connected with, or that both include and are connected with one or more processors, controllers, and/or other hardware logic-based devices. Additionally or alternatively, the controller circuit 1305 may execute instructions stored on a tangible and non-transitory computer readable medium (e.g., a memory 1364).

The table controller 1334 may move the patient table 1320 to position the subject 1301 relative to the imaging detectors 1302. The patient table 1320 may be moved in up-down directions, in-out directions, and right-left directions, for example. The detector controller 1336 may control movement of each of the imaging detectors 1302 to move together as a group or individually. The detector controller 1336 also may control movement of the imaging detectors 1302 in some embodiments to move closer to and farther from a surface of the subject 1301, such as by controlling translating movement of the detector carriers 1316 linearly towards or away from the subject 1301 (e.g., sliding or telescoping movement). Optionally, the detector controller 1336 may control movement of the detector carriers 1316 to allow movement of the detector array 1306 or 1308. For example, the detector controller 1336 may control lateral movement of the detector carriers 1316 illustrated by the T arrow (and shown as left and right). In various embodiments, the detector controller 1336 may control the detector carriers 1316 or the support members 1312 to move in different lateral directions. Detector controller 1336 may control the swiveling motion of detectors 1302 together with their collimators 1322. In some embodiments, detectors 1302 and collimators 1322 may swivel or rotate around an axis.

The pivot controller 1338 may control pivoting or rotating movement of the detector units 1314 at ends of the detector carriers 1316 and/or pivoting or rotating movement of the detector carrier 1316. For example, one or more of the detector units 1314 or detector carriers 1316 may be rotated about at least one axis to view the subject 1301 from a plurality of angular orientations to acquire, for example, 3D image data in a 3D SPECT or 3D imaging mode of operation. The collimator controller 1340 may adjust a position of an adjustable collimator, such as a collimator with adjustable strips (or vanes) or adjustable pinhole(s).

It should be noted that motion of one or more imaging detectors 1302 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1336 and pivot controller 1338 may be combined to provide the different movements described herein.

Prior to acquiring an image of the subject 1301 or a portion of the subject 1301, the imaging detectors 1302, gantry 1304, patient table 1320 and/or collimators 1322 may be adjusted, such as to first or initial imaging positions, as well as subsequent imaging positions. The imaging detectors 1302 may each be positioned to image a portion of the subject 1301. Alternatively, for example in a case of a small size subject 1301, one or more of the imaging detectors 1302 may not be used to acquire data, such as the imaging detectors 1302 at ends of the detector arrays 1306 and 1308, which as illustrated in FIG. 13 are in a retracted position away from the subject 1301. Positioning may be accomplished manually by the operator and/or automatically, which may include using, for example, image information such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector units 1314 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1302, gantry 1304, patient table 1320, and/or collimators 1322 are positioned, one or more images, such as three-dimensional (3D) SPECT images are acquired using one or more of the imaging detectors 1302, which may include using a combined motion that reduces or minimizes spacing between detector units 1314. The image data acquired by each imaging detector 1302 may be combined and reconstructed into a composite image or 3D images in various embodiments.

In one embodiment, at least one of detector arrays 1306 and/or 1308, gantry 1304, patient table 1320, and/or collimators 1322 are moved after being initially positioned, which includes individual movement of one or more of the detector units 1314 (e.g., combined lateral and pivoting movement) together with the swiveling motion of detectors 1302. For example, at least one of detector arrays 1306 and/or 1308 may be moved laterally while pivoted. Thus, in various embodiments, a plurality of small sized detectors, such as the detector units 1314 may be used for 3D imaging, such as when moving or sweeping the detector units 1314 in combination with other movements.

In various embodiments, a data acquisition system (DAS) 1360 receives electrical signal data produced by the imaging detectors 1302 and converts this data into digital signals for subsequent processing. However, in various embodiments, digital signals are generated by the imaging detectors 1302. An image reconstruction device 1362 (which may be a processing device or computer) and the memory 1364 may be provided in addition to the controller circuit 1305. It should be noted that one or more functions related to one or more of data acquisition, motion control, data processing and image reconstruction may be accomplished through hardware, software and/or by shared processing resources, which may be located within or near the medical imaging system 1300, or may be located remotely. DAS 1360 receives the acquired images from detectors 1302 together with the corresponding lateral, vertical, rotational and swiveling coordinates of gantry 1304, support members 1312, detector units 1314, detector carriers 1316, and detectors 1302 for accurate reconstruction of an image including 3D images and their slices.

In an embodiment, a method (e.g., for object detection of a patient) is provided. The method includes acquiring triplets representing line of sights between a plurality of receive diodes and light emitting diodes (LEDs) positioned along a circumference of a gantry with respect to one or more objects of a patient. The method includes identifying a number of the one or more objects based on a number of triplets for one of the LEDs. When a single object is identified, determining a shape of the single object based on a reference point within the single object and line of sights adjacent to the single object. Alternatively, when a plurality of objects are identified, utilizing the line of sights to identify shapes of the plurality of objects.

Optionally, the determining operation includes selecting a first line of sight based on a distance between the reference point and the lines of sight, and identifying intersection points for second and third line of sights relative to the first line of sight. Additionally or alternatively, the method includes identifying opposing ends of the second line of sight, selecting one of the opposing ends between the reference point that does not intersect the first line of sight. Optionally, the utilizing operation includes generating images based on the line of sights. The images represent the triplets such that outside the plurality of objects represents zero and within the plurality of objects is one. Additionally or alternatively, the method includes combining the images together to identify the shapes of the plurality of objects. Optionally, the method includes identifying a mismatch object relative to the identifying operation, selecting triplets that are blocked by the plurality of objects, and identifying the triplets that are blocked by the mismatch object and corresponding intersection points within the mismatch object. Optionally, the method includes determining a number of intersection points within a predetermined radius, and identifying a position of the mismatch object based on the number of intersection points within the predetermined radius. Additionally or alternatively, wherein the predetermined radius is one centimeter.

In an embodiment, a medical imaging system is provided. The medical imaging system includes plurality of diodes and light emitting diodes (LEDs) disposed about a circumference of a gantry. The system includes at least one processor operably coupled to the plurality of diodes and LEDs. The at least one processor configured to acquire triplets representing line of sights between the plurality of diodes and LEDs with respect to one or more objects. The at least one processor is configured to identify a number of the one or more objects based on a number of triplets for one of the LEDs. When a single object is identified the at least one processor is configured to determine a shape of the single object based on a reference point within the single object and line of sights adjacent to the single object. When a plurality of objects are identified the at least one processor is configured to utilize the lines of sights to identify shapes of the plurality of objects.

Optionally, the at least one processor is configured to select a first line of sight based on a distance between the reference point and the lines of sight, and identify intersection points for second and third line of sights relative to the first line of sight. Additionally or alternatively, the at least one processor is configured to identify opposing ends of the second line of sight, selecting one of the opposing ends between the reference point that does not intersect the first line of sight. Optionally, the at least one processor is configured to generate images based on the line of sights. The images representing the triplets such that outside the plurality of objects represents zero and within the plurality of objects is one. Additionally or alternatively, the at least one processor is configured to combine the images together to identify the shapes of the plurality of objects. Optionally, the at least one processor is configured to identify a mismatch contour relative to the identifying operation, select triplets that are blocked by the plurality of contours, and identify the triplets that are blocked by the mismatch contour and corresponding intersection points within the mismatch object. Additionally or alternatively, the at least one processor is configured to determine a number of intersection points within the mismatch object within a predetermined radius, and select a position of the mismatch object based on the number of intersection points within the predetermined radius. Optionally, the predetermined radius is one centimeter.

In an embodiment, a tangible and non-transitory computer readable medium is provided. The tangible and non-transitory computer readable medium includes one or more programmed instructions configured to direct one or more processors. The one or more processors are configured to acquire triplets representing line of sights between a plurality of diodes and light emitting diodes (LEDs) positioned along a circumference of a gantry with respect to one or more objects. The one or more processors are configured to identify a number of the one or more objects based on a number of triplets for one of the LEDs. When a single contour is identified, the one or more processors are configured to determine a shape of the single object based on a reference point within the single object and lines of sight adjacent to the single object. When a plurality of objects are identified, the one or more processors are configured to utilize the lines of sights to identify shapes of the plurality of objects.

Optionally, the one or more processors are further directed to: select a first line of sight based on a distance between the reference point and the lines of sight; identify intersection points for second and third line of sights relative to the first line of sight; identify opposing ends of the second line of sight; and select one of the opposing ends between the reference point that does not intersect the first line of sight. Optionally, the images represent the triplets such that outside the plurality of objects represents zero and within the plurality of objects is one.

Optionally, the one or more processors are further directed to: identify a mismatch object relative to the identifying operation; select triplets that are blocked by the plurality of objects; identify the triplets that are blocked by the mismatch object and corresponding intersection points within the mismatch object; determine a number of intersection points within the mismatch object within a predetermined radius; and select a position of the mismatch object based on the number of intersection points within the predetermined radius.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
   acquiring triplets representing line of sights between a plurality of receive diodes and light emitting diodes (LEDs) positioned along a circumference of a gantry with respect to one or more objects of a patient;
   identifying a number of the one or more objects based on a number of triplets for one of the LEDs;
   i) when a single object is identified, determining a shape of the single object based on a reference point within the single object and line of sights adjacent to the single object; and
   ii) when a plurality of objects are identified, utilizing the line of sights to identify shapes of the plurality of objects.

2. The method of claim 1, wherein the determining operation includes selecting a first line of sight based on a distance between the reference point and the lines of sight, and identifying intersection points for second and third line of sights relative to the first line of sight.

3. The method of claim 2, further comprising forming a first line from the reference point to a first end of the second line of sight, forming a second line from the reference point to a second end of the second line of sight opposed to the first end, determining which of the first line or second line crosses the first line of sight, and selecting the corresponding end of the line that does not intersect the first line of sight.

4. The method of claim 1, wherein the utilizing operation includes generating images based on the line of sights, wherein the images represent the triplets such that outside the plurality of objects represents zero and within the plurality of objects is one.

5. The method of claim 4, further comprising combining the images together to identify the shapes of the plurality of objects.

6. The method of claim 1, further comprising identifying a mismatch object relative to the identifying operation, selecting triplets that are blocked by the plurality of objects, and identifying the triplets that are blocked by the mismatch object and corresponding intersection points within the mismatch object.

7. The method of claim 6, further comprising determining a number of intersection points within a predetermined radius, and identifying a position of the mismatch object based on the number of intersection points within the predetermined radius.

8. The method of claim 7, wherein the predetermined radius is one centimeter.

9. A medical imaging system, comprising:
  plurality of receive diodes and light emitting diodes (LEDs) disposed about a circumference of a gantry;
  at least one processor operably coupled to the plurality of diodes and LEDs, the at least one processor configured to:
  acquire triplets representing line of sights between the plurality of receive diodes and LEDs with respect to one or more objects;
  identify a number of the one or more objects based on a number of triplets for one of the LEDs;
  i) when a single object is identified, determine a shape of the single object based on a reference point within the single object and line of sights adjacent to the single object;
  ii) when a plurality of objects are identified, utilize the lines of sights to identify shapes of the plurality of objects.

10. The medical imaging system of claim 9, wherein the at least one processor is configured to select a first line of sight based on a distance between the reference point and the lines of sight, and identify intersection points for second and third line of sights relative to the first line of sight.

11. The medical imaging system of claim 10, wherein the at least one processor is configured to form a first line from the reference point to a first end of the second line of sight, form a second line from the reference point to a second end of the second line of sight opposed to the first end, determine which of the first line or second line crosses the first line of sight, and select the end of the corresponding line that does not intersect the first line of sight.

12. The medical imaging system of claim 9, wherein the at least one processor is configured to generate images based on the line of sights, the images representing the triplets such that outside the plurality of objects represents zero and within the plurality of objects is one.

13. The medical imaging system of claim 12, wherein the at least one processor is configured to combine the images together to identify the shapes of the plurality of objects.

14. The medical imaging system of claim 9, wherein the at least one processor is configured to identify a mismatch object relative to the identifying operation, select triplets that are blocked by the plurality of objects, and identify the triplets that are blocked by the mismatch object and corresponding intersection points within the mismatch object.

15. The medical imaging system of claim 14, wherein the at least one processor is configured to determine a number of intersection points within the mismatch object within a predetermined radius, and select a position of the mismatch object based on the number of intersection points within the predetermined radius.

16. The medical imaging system of claim 15, wherein the predetermined radius is one centimeter.

17. A tangible and non-transitory computer readable medium comprising one or more programmed instructions configured to direct one or more processors to:
  acquire triplets representing line of sights between a plurality of receive diodes and light emitting diodes (LEDs) positioned along a circumference of a gantry with respect to one or more objects;
  identify a number of the one or more objects based on a number of triplets for one of the LEDs;
  i) when a single object is identified, determine a shape of the single object based on a reference point within the single object and lines of sight adjacent to the single object; and
  ii) when a plurality of objects are identified, utilize the line of sights to identify shapes of the plurality of objects.

18. The tangible and non-transitory computer readable medium of claim 17, wherein the one or more processors are further directed to:
  select a first line of sight based on a distance between the reference point and the lines of sight;
  identify intersection points for second and third line of sights relative to the first line of sight;
  form a first line from the reference point to a first end of the second line of sight;
  form a second line from the reference point to a second end of the second line of sight opposed to the first end;
  determine which of the first line or second line cress the first line of sight; and
  select the corresponding end of the line that does not intersect the first line of sight.

19. The tangible and non-transitory computer readable medium of claim 17, wherein the objects, represent the triplets such that outside the plurality of objects represents zero and within the plurality of objects is one.

20. The tangible and non-transitory computer readable medium of claim 17, wherein the one or more processors are further directed to:
  identify a mismatch object relative to the identifying operation;
  select triplets that are blocked by the plurality of objects;
  identify the triplets that are blocked by the mismatch object and corresponding intersection points within the mismatch object;
  determine a number of intersection points within the mismatch object within a predetermined radius; and
  select a position of the mismatch object based on the number of intersection points within the predetermined radius.

* * * * *